United States Patent [19]

James

[11] 4,450,435
[45] May 22, 1984

[54] ANALOG DEBRIS ALARM

[75] Inventor: Bobby D. James, 7184 W. 2nd La., Hialeah, Fla. 33014

[73] Assignee: Bobby Dencil James, Hialeah, Fla.

[21] Appl. No.: 325,789

[22] Filed: Nov. 30, 1981

[51] Int. Cl.³ .................. G08B 29/00; G01N 27/00
[52] U.S. Cl. ............................... 340/511; 324/71.1
[58] Field of Search ............ 340/627, 511, 512, 659, 340/661; 324/71.1, 71.4, 439; 364/555; 377/10, 12

[56] References Cited

U.S. PATENT DOCUMENTS

| | | | |
|---|---|---|---|
| 2,656,508 | 10/1953 | Coulter | 324/71.1 |
| 3,259,842 | 7/1966 | Coulter et al. | 377/12 |
| 3,259,891 | 7/1966 | Coulter et al. | 377/12 |
| 3,444,463 | 5/1969 | Coulter et al. | 324/71.1 |
| 3,700,867 | 10/1972 | Gogg | 364/555 |
| 3,733,547 | 5/1973 | Coulter et al. | 324/71.1 |
| 3,757,213 | 9/1973 | Coulter et al. | 324/71.1 |
| 3,801,901 | 4/1974 | Hogg | 324/71.1 |
| 3,820,019 | 6/1974 | Doty et al. | 324/71.1 |
| 3,882,385 | 5/1975 | Coulter et al. | 324/71.1 |
| 4,001,678 | 1/1977 | Berg | 324/71.1 |
| 4,212,175 | 10/1983 | Maynarez | 324/71.1 |

Primary Examiner—John W. Caldwell, Sr.
Assistant Examiner—Daniel Myer
Attorney, Agent, or Firm—Gerald R. Hibnick

[57] ABSTRACT

A debris alarm device for use with a particle analyzing apparatus of the Coulter ® type generates discrete particle pulses in response to liquid suspended particles passing through a sensing aperture, the debris alarm comprising threshold circuitry for generating a threshold pulse for each particle pulse; circuitry for generating, for each threshold pulse, a normal pulse of predetermined duration; a first current source and a second current source for providing currents of opposite polarity to an integrator, when said current sources are triggered, respectively, by the threshold pulses and the normal pulses; and debris indicator circuitry, including an alarm, for determining when the output voltage of the integrator, which initially is set to zero, falls out of a predetermined voltage window. In an alternative embodiment, the same polarity first and second currents are fed to separate integrators and the debris indicating circuit detects when the outputs of the two integrators exceed a preset relative percent difference and thereafter enables the alarm.

9 Claims, 5 Drawing Figures

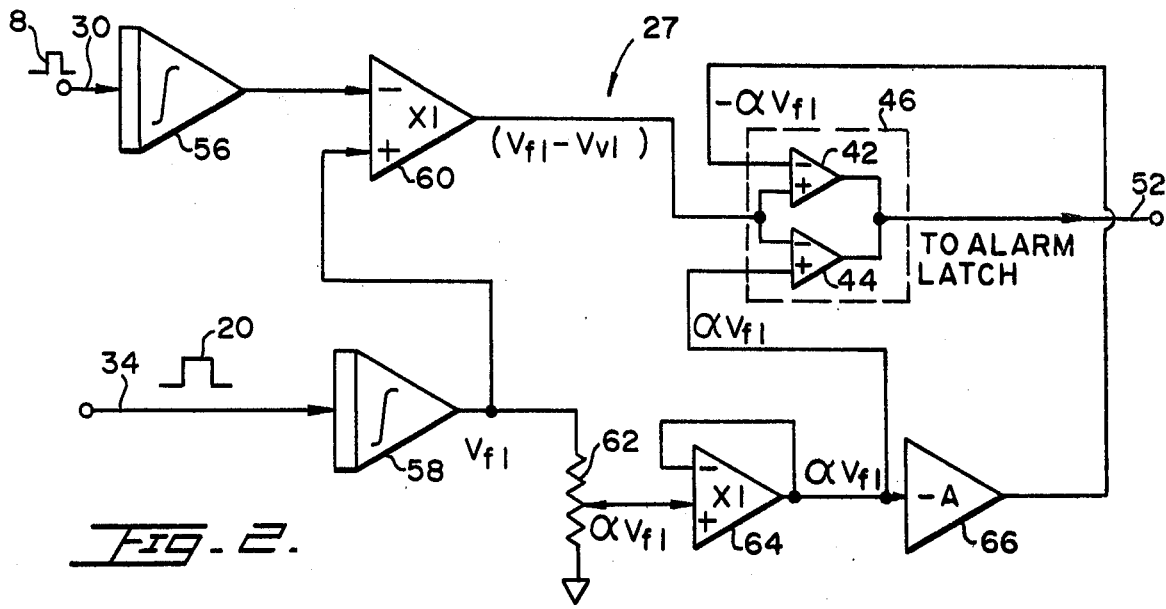
_Fig. 2._
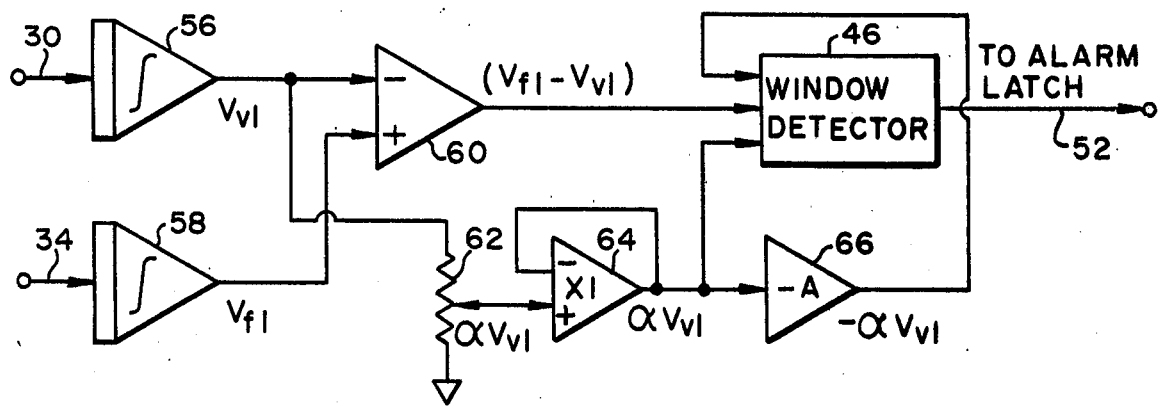
_Fig. 3._
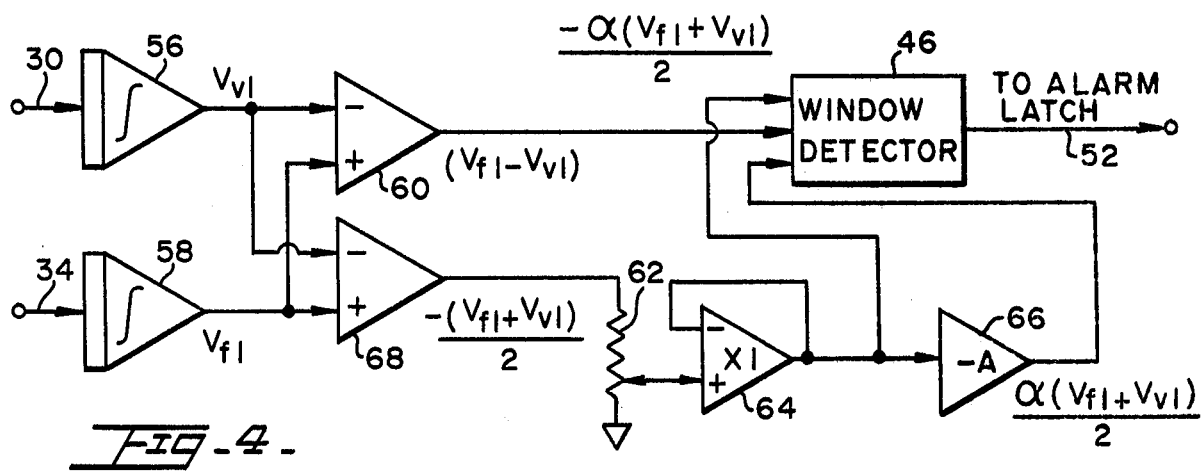
_Fig. 4._

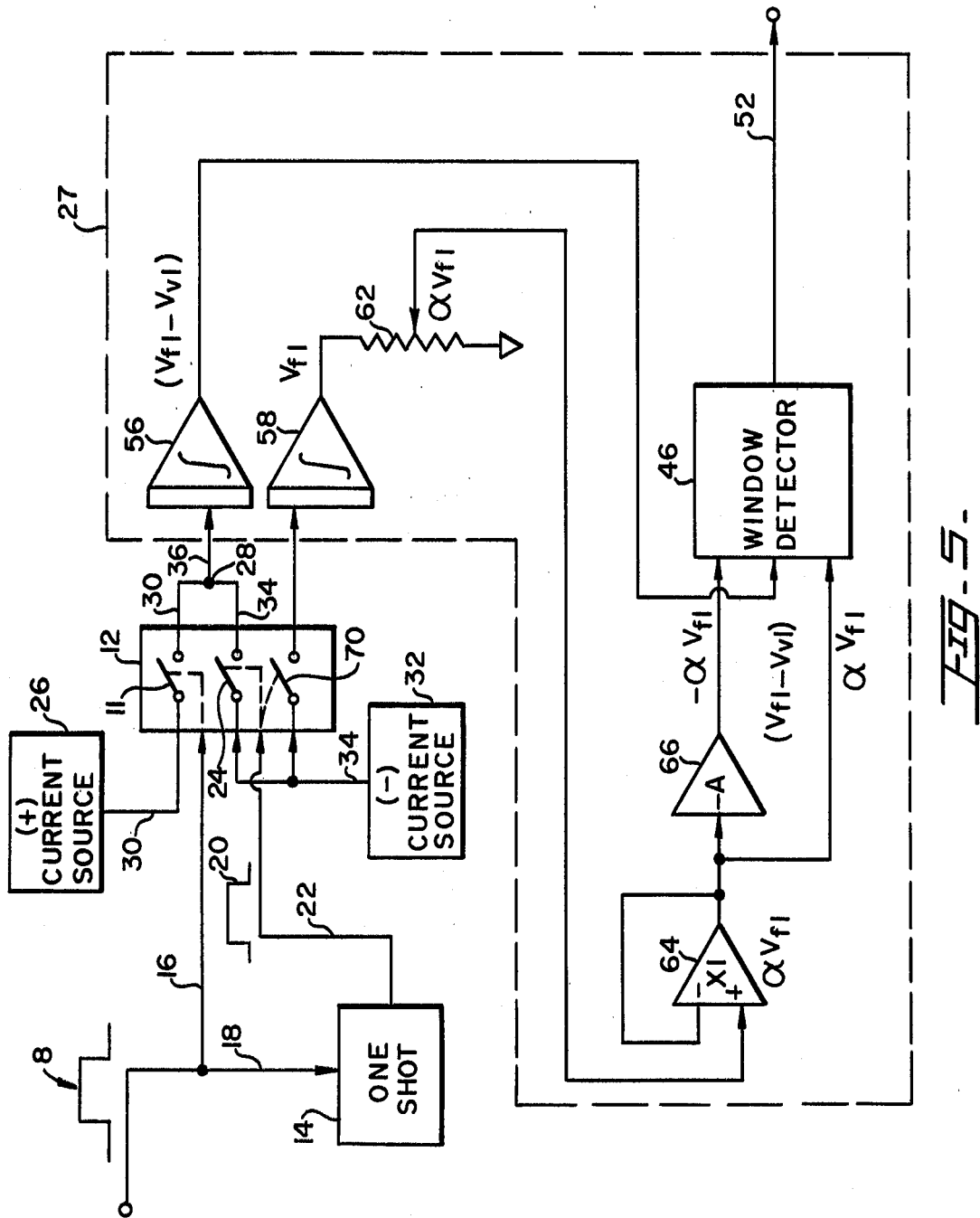

ANALOG DEBRIS ALARM

BACKGROUND OF THE INVENTION

1. Field of the Invention

The present invention relates generally to particle analyzing apparatuses and more particularly is concerned with a circuit arrangement incorporated into such analyzing apparatus for detecting abnormal functioning of the particle sensing function of the analyzing apparatus caused by some obstruction thereof.

2. Description of the Prior Art

In U.S. Pat. No. 3,259,891 to Coulter et al. there is disclosed a debris alarm for a practice analyzing apparatus wherein the particle pulses are collected above a higher than normal threshold. The portions of the pulses above this threshold are converted to constant amplitude pulses, which are integrated to obtain their widths. If a given pulse width reaches some predetermined width, an alarm condition is triggered.

In particle sensing undertaken in the above described particle analyzer of the Coulter ® type, there are several possible situations where debris in the liquid sample suspension being processed can affect the particle count. First, debris that passes through the sensing aperture generally results in a long pulse, which is usually a result of the debris being long in length, or very large in size compared to normal particles. This condition results in the loss of counts for particles during the time period in which the debris is passing through the orifice. Secondly, the debris can partially block off the sensing aperture, resulting in particle pulses that have abnormally short widths. Such a condition results in bad mean cell volume measurements, due to the reduction of the aperture's diameter and off axis trajectories of the particles through the aperture. Moreover, in systems having positive displacement fluid movement through the aperture, a partial blockage will increase the velocity of the sample flow through the aperture, thereby narrowing the widths of the particle pulses. As a result, particle pulses can be generated that are too narrow for a proper response by an amplifier in the detection circuitry of the particle analyzer. Additionally, various sources of electronic noise can create narrow pulses that can be confused as particle pulses.

In view of the possible debris condition described above, it can be seen that U.S. Pat. No. 3,259,891 is only able to detect abnormally long pulses on a pulse-by-pulse basis. Hence, this design is deficient in the following ways. This design is not able to detect pulses that are abnormally short, such as those caused by electronic noise or by a partially blocked aperture. Secondly, the design of the prior art requires that the pulse exceed a relatively high threshold level, meaning that some debris may generate particle pulses, yet not exceed this threshold. Third, the technique only examines pulses on an individual basis, and does not provide a benchmark or reference point for determining how much debris exists in the processed sample. In other words, a single piece of debris might trigger the alarm, yet it might be the only significant debris in the sample.

Accordingly, it can be seen that there is a need in the particle analyzer art to have a debris alarm which can detect pulses which are both too short and too long and after such detection, determine how many bad pulses there are with respect to some benchmark or reference number.

SUMMARY OF THE INVENTION

The invention provides a debris alarm for an electronic particle analyzing apparatus of the Coulter ® type wherein a particulate suspension and an electronic current are simultaneously passed through a particle sensing aperture, so as to generate discrete particle pulses. Threshold circuitry generates a threshold pulse for each particle pulse which exceeds a predetermined threshold. Each threshold pulse causes normal pulse circuitry to generate a normal pulse of a predetermined, constant duration which substantially corresponds to the duration of threshold pulses for normal particle pulses. Each threshold pulse enables a first current source to generate a first current while receiving the threshold pulse and each normal pulse enables a second current source to generate a second current while receiving the normal pulse. Comparative circuitry means are provided for comparing the cumulative quantity of the first current to that of the second current and if the compared cumulative quantities differ by a predetermined amount, an alarm is enabled to notify the operator of this condition.

Hence, if there are too many threshold pulses that are too short or too long relative to the normal pulses, their cumulative impart, depending upon how short and how long are the abnormal threshold pulses, will eventually enable the alarm. Consequently, for example, when there is an unacceptable quantity of debris in the sample passing through the sensing aperture and/or there is a partial or complete blockage of the sensing aperture, the operator will be notified.

BRIEF DESCRIPTION OF THE DRAWINGS

Further objects and advantages of the present invention will become apparent as the following description proceeds, taken in conjunction with the accompanying drawing in which:

FIG. 2 is an electrical schematic diagram of another embodiment of the debris alarm device;

FIG. 3 is an electrical schematic diagram of yet another embodiment of the debris alarm device;

FIG. 4 is an electrical schematic diagram of yet another embodiment of the debris alarm device;

FIG. 5 is an electrical schematic diagram of yet another embodiment of the debris alarm device.

DETAILED DESCRIPTION OF THE EMBODIMENT

Figure 1:
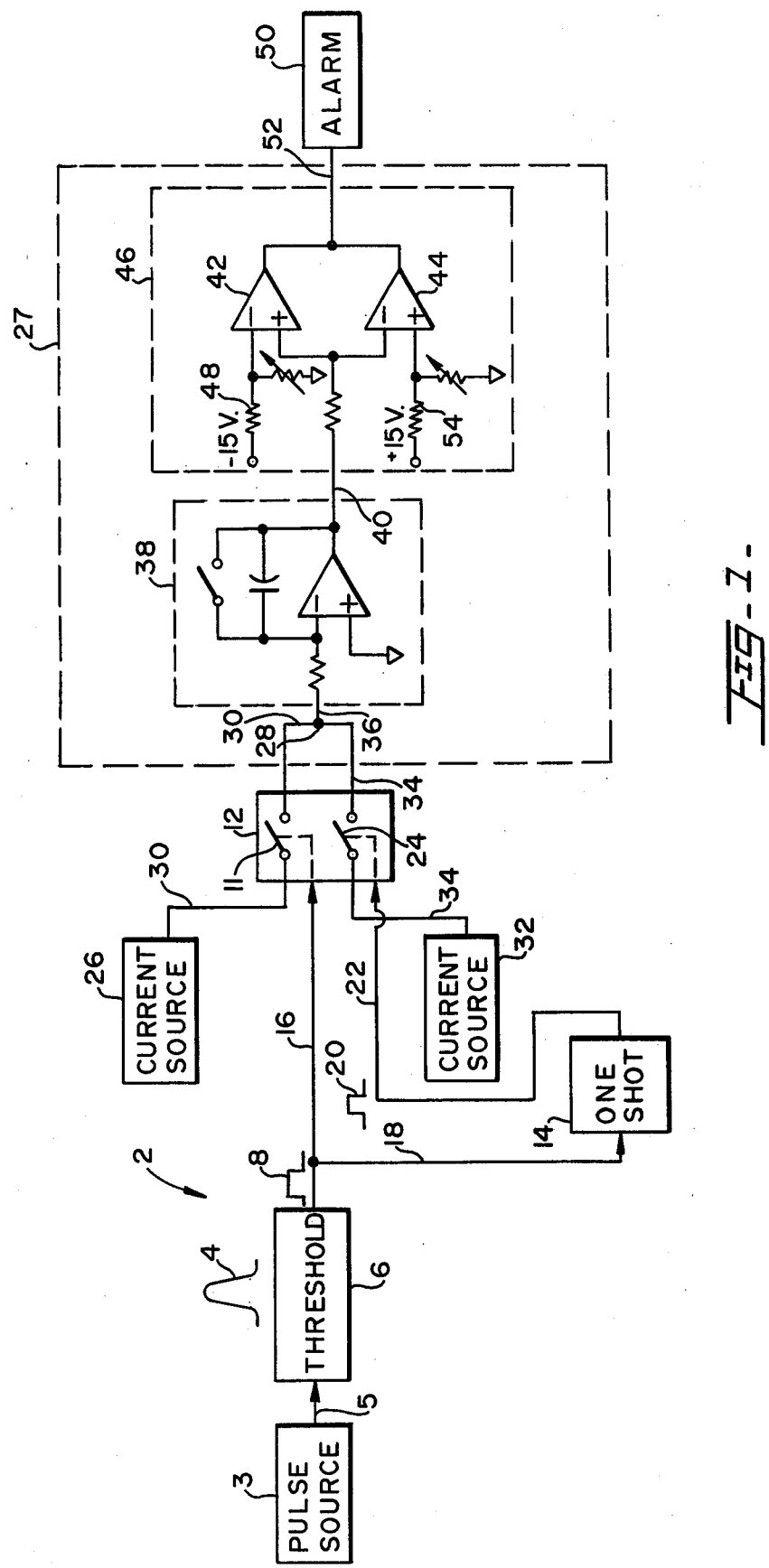
FIG. 1 is an electrical schematic diagram of the first embodiment of a debris alarm device embodying the invention.

Referring to FIG. 1, there is shown a debris alarm device embodying the invention and identified generally by the referenced number 2. A pulse source 3 comprises a particle sensing aperture and related circuitry of a Coulter ® type particle detector, such as shown and described in U.S. Pat. Nos. 2,656,508 and 3,259,842, wherein particle pulses 4 are developed in response to the passage of particles in a particulate suspension through the sensing zone of the particle sensing aperture. More specifically, an electric current passes through the particle sensing aperture and particle pulses are produced as a result of the modulation of this current by the passage of particles through the particle sensing aperture. Each pulse amplitude is approximately proportional to the size or volume of the pulse producing particle. Although the debris alarm embodying the present invention is utilizable with all types of Coulter ® type apparatuses, it is particularly useful with those designs having a constant volume displacement per unit time pump to draw the sample suspension containing particles through the particle sensing aperture, as shown in U.S. Pat. No. 4,001,678.

The particle pulses 4, developed by the pulse source 3, are coupled via an electrical conductor 5 to pulse threshold means in the form of a threshold circuit 6. Threshold pulses 8 of a fixed amplitude are fed from the threshold circuit 6 to a first switch 11 of a dual field effect transistor (FET) switch means 12 and normal pulse generating means in the form of a one shot 14 by way of electrical conductors 16 and 18, respectively.

The one shot 14 is triggered by the falling (trailing) edge of each threshold pulse to generate a fixed length pulse 20 of a predetermined duration. The one shot 14 is set to provide the pulses 20 with a duration that approximates the average duration of the threshold pulses 8 generated by normal particle pulses 4. Such a length duration can be empirically determined from cumulative statistical data of pulse lengths for threshold pulses 8 at a predetermined threshold level for the threshold circuit 6. The fixed length pulses are fed via an electrical conductor 22 to a second switch 24 of the dual FET switch means 12. The first switch 11 and the second switch 24 are closed while receiving the threshold pulses 8 and the fixed length pulses 20, respectively. Hence, the first current source 26 and first switch 11 define a first current generating means and the second current source 32 and second switch 24 define a second current generating means. An output of a first current source 26 is provided through the first switch 11 by way of an electrical conductor 30. An output of a second current source 32 is provided through the second switch 24 by way of an electrical conductor 34. The above-described portion of the debris alarm 2 remains the same in each of the hereinafter described embodiments, with the exception of differing combinations of polarities for the currents provided by the current sources 32.

A first embodiment of a current comparing means 27, for comparing the currents from the sources 26 and 32, is shown in FIG. 1. The conductors 30 and 34 are electrically coupled to a summing junction 28. The summing junction 28 is electrically coupled by way of an electrical conductor 36 to an integrator 38.

In operation, a given threshold pulse 8 causes the first current source 26 to generate a positive current to "pump down" the integrator 38 during the duration of a given threshold pulse 8. At the end of that threshold pulse 8, the one shot 14 causes the second current source 32 to generate a negative current to "pump up" the integrator 38. The amplitude of the positive and negative currents are the same. When a threshold pulse 8 of normal duration is received, the integrator 38 will typically pump up and then pump down by approximately the same amount, with the net change in the integrator being relatively small. If a threshold pulse 8 of abnormal duration is generated, be it too long or too short, the net change in the integrator 38 will be in a positive or negative direction. For instance, when the sensing aperture of the pulse source 3 is partially plugged, the threshold pulses 8 of abnormally short duration will be generated, causing the integrator 38 to be pumped in a positive direction. Likewise, when large debris particles pass through the sensing aperture and generate threshold pulses 8 that are abnormally long, the integrator 38 will be pumped in a negative direction.

The output of the integrator 38 is electrically coupled via an electrical conductor 40 to the inputs of a pair of comparators 42 and 44 which form a window detector 46. More specifically, an upper threshold value is set by applying a predetermined voltage through a divider network 48 to one input of the comparator 42. The output signal from the integrator 38 is fed to the other input of the comparator 42, and when it exceeds the upper threshold value, an enabling signal is applied to an alarm 50 by way of an electrical conductor 52, so as to activate the same to indicate a debris condition. Likewise, the comparator 44 has a lower threshold value set by applying a predetermined voltage through a voltage divider network 54 to one input of the comparator 44. The output signal from the integrator 38 is fed to the other input of the comparator 44 and when it exceeds the preset lower threshold value, an enabling signal is sent to the alarm 50 by way of the conductor 52. By virtue of this arrangement, when the pulse source 3 generates abnormal pulses and the integrator 38 is pumped in a positive or negative direction by an amount to exceed the upper or lower thresholds, respectively, an alarm condition will be indicated to the operator.

The above-described embodiment of the current comparing means 27 has the limitation of being limited in range, due to the detector window 46 having preset fixed voltage thresholds. Contrary to this, the next three alternative embodiments of the current comparing means 27 have variable thresholds for triggering the debris alarm 50. In each of these embodiments, the rest of the debris alarm device 2 circuitry remains essentially the same as shown in FIG. 1, except the polarities of the two current sources 26, as previously mentioned, are preferably of the same polarity and preferably both the current source 26 and the one shot 14 are triggered at the same time, for example, by the leading edge of the threshold pulse 8.

FIG. 2 illustrates a second embodiment of the current comparing means 27, wherein there is a pair of integrators 56 and 58 which receive, respectively, the variable length threshold pulses 8, by way of the conductor 30, and the fixed length pulses 20, by way of the conductor 34. The integrator 56 generates an output voltage $V_{vl}$ representative of the total cumulative charge of variable length pulses 8 and integrator 58 generates an output voltage $V_{fl}$ representative of the total cumulative charges of the fixed length pulses 20. A pair of inputs of a difference amplifier 60 are electrically coupled to the outputs of the integrators 56 and 58, so that the amplifier 60 generates an output voltage equal to the difference in the output voltage of the integrators 56 and 58, i.e., $V_{fl} - V_{vl}$. The output of the integrator 58 is also fed to a variable potentiometer 62, which multiplies the output voltage $V_{fl}$ by a preselected percentage $\alpha$, as shown in FIG. 2 ($\alpha V_{fl}$), such that the output voltage of the integrator 58 can be adjusted from 0 to 100% for presentation to a buffer amplifier 64. The potentiometer 62 is coupled to the unity gain buffer amplifier 64 to give the same output $\alpha V_{fl}$. The output voltage $\alpha V_{fl}$ of the buffer amplifier 64 is fed to the positive terminal of the comparator 44 of the window detector 46 and is also fed to an inverting amplifier 66 of unity gain, which provides an output voltage ($-\alpha V_{fl}$) to the negative terminal of the comparator 42 of the detector window 46. The output of the differential amplifier 60 ($V_{fl} - V_{vl}$) is coupled to the positive terminal of the comparator 42 and the negative terminal of the comparator 44. Hence, the upper threshold voltage of the window detector 46 becomes $\alpha V_{fl}$ and the lower threshold voltage becomes $-\alpha V_{fl}$. In other words, the thresholds consist of a preset ratio or percentage of the output voltage $V_{fl}$, which is representative of the total fixed length pulses generated, and the alarm 50 will be activated when the following relationship is satisfied:

$$\alpha > (V_{fl} - V_{vl})/V_{fl} > -\alpha$$

Hence, when the ratio of the difference in the voltages generated by the variable length and fixed length pulses 8 and 20 to the voltage generated by the fixed length pulses 20 exceeds the preset percentage $\alpha$, then the alarm 50 (not shown in FIG. 2) is triggered. In summary, the thresholds for the triggering signal to the debris alarm 50 are referenced to the cumulative charge of the fixed length pulses 20.

In FIG. 3, another alternative embodiment of the current comparing means 27 is shown, wherein the threshold voltages for the window detector 46 are referenced to the cumulative charge of the threshold pulses 20, i.e., the output voltage $V_{vl}$. More specifically, the circuitry is the same in design and operation as that shown in FIG. 2, except the output of the integrator 56 is electrically coupled to the potentiometer 62, instead of, as shown in FIG. 2, having the output of integrator 58 coupled thereto. By virtue of this modification, the threshold voltages become $\alpha V_{vl}$ and $-\alpha V_{vl}$, a percentage of the output voltage generated by the cumulative charge i.e., provided by the threshold pulse 8. Hence, the alarm 50 will be activated when the following mathematical relationship exists:

$$\alpha > (V_{fl} - V_{vl})/V_{vl} > -\alpha$$

In FIG. 4, another alternative embodiment of the current comparing means 27 is shown wherein the threshold voltages for the window detector 46 are referenced to an average of the voltages generated by the cumulative charge from the threshold pulses 8 and the fixed length pulses 20. The circuitry is the same in design and operation as that shown in FIG. 2, except instead of coupling the output of integrator 58 directly to the potentiometer 62, the output voltage $V_{vl}$ from integrator 56 and the output voltage $V_{fl}$ from integrator 58 is electrically coupled to an adder amplifier 68. The adder amplifier generates an output voltage equal to the following:

$$-(V_{fl} + V_{vl})/2$$

The output of the adder amplifier 68 is coupled to the potentiometer 62, which in turn causes the threshold voltages to be the positive and negative values of the following:

$$\alpha (V_{fl} + V_{vl})/2$$

Hence, the alarm 50 will be activated when the following mathematical relationship exists:

$$\alpha > \frac{(V_{fl} - V_{vl})}{\frac{(V_{fl} + V_{vl})}{2}} > -\alpha$$

FIG. 5 shows an alternative embodiment of the debris alarm device 2, wherein the circuit design of FIG. 1 is modified to accomplish the objectives of the embodiments of FIGS. 2 through 4, without the need for the difference amplifiers shown in FIGS. 2 through 4. More specifically, the circuitry to the left of the current comparing means 27 is the same in design and operation as shown in FIG. 1, except the output of current source 32, which is negative, is coupled to the input of an additional switch, third switch 70, which is part of switch means 12. Like the second switch 24, the third switch 70 is switched closed when a fixed length pulse 20 is received from the one shot 14, and is open when no pulses are being received. Preferably, the one shot is triggered on the trailing edge of the threshold pulse 8. The integrator 56 generates an output voltage equal to $(V_{fl} - V_{vl})$. More specifically, the positive current source 26 is switched in by the threshold pulse 8 and when the trailing edge of the threshold pulse 8 arrives, the positive current source 26 is switched out and the negative current source 34 is switched in, giving as a net result the output voltage $(V_{fl} - V_{vl})$. Likewise, the integrator 58 generates an output voltage equal to $V_{fl}$. A percentage of the output voltage from the integrator 58, via potentiometer 62, is electrically coupled to the buffer amplifier 64 and the output voltage from the integrator 56 is coupled to the window detector 46. The remainder of the circuit is the same in design and operation as shown in FIG. 2, and the output voltages are used to generate threshold voltages for the detector window of $\alpha V_{fl}$ and $-\alpha V_{fl}$. It will be clear to those skilled in the art that the current comparing means 27 of FIG. 5 can be modified to also obtain the threshold values for the window detector that are shown in the embodiments of FIGS. 3 and 4.

Although particular embodiments of the invention have been shown and described herein, there is no intention thereby to limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A debris alarm for use with a particle analyzing apparatus for studying particles in suspension, said apparatus including a particle sensing aperture through which said particles in suspension are passed, means for passing an electric current through said aperture simultaneously with passage of a particle through said aperture, and detecting means responsive to impedance variations for generating a discrete particle pulse with the passage of said particle through said aperture, said debris alarm comprising:

pulse threshold means, being electrically coupled to said detecting means, for generating a threshold pulse for each particle pulse which exceeds a predetermined threshold level, said threshold pulse having a duration which is a function of the width of said particle pulse at said predetermined threshold level;

fixed length pulse generating means, being electrically coupled to said pulse threshold means, for generating a fixed length pulse of predetermined duration substantially corresponding to that of said threshold pulses for normal said particle pulses, said fixed length pulse generating means operative to generate one said fixed length pulse for each said threshold pulse;

first current generating means, being electrically coupled to said pulse threshold means, for providing an electrical first current in an amount directly proportional to the charge of said threshold pulses;

second current generating means, being electrically coupled to said fixed length pulse generating means, for providing an electrical second current in an amount directly proportional to the charge of said fixed length pulses;

current comparing means, including different means, for receiving said first currents and said second currents, for accumulating the electrical charges of said currents and for providing as an output a difference voltage proportional to the difference in the cumulative charges of said first currents and said second currents;

said current comparing means further including window detector means, being electrically coupled to said difference means, for determining when said difference voltage exceeds a positive upper threshold voltage or falls below a negative lower threshold voltage, said upper and lower threshold voltages defining a predetermined comparison window; and debris indicator means, being electrically coupled to said window detector means, for indicating that said difference voltage has fallen out of said predetermined comparison window.

2. The debris alarm according to claim 1, wherein said pulse threshold means has an input electrically coupled to an output of said detecting means and an output electrically coupled to the inputs of both said first current generating means and said fixed length pulse generating means, said fixed length pulse generating means having an output electrically coupled to the input of said second current generating means, each of said current generating means having an output electrically coupled to the input of said difference means, said difference means having an output electrically coupled to an input of said window detector means, said window detector means having an output electrically coupled to said debris indicator means.

3. The debris alarm according to claim 1, wherein said first current generating means is enabled by each said threshold pulse to generate said first current during the duration of each said threshold pulse and said second current generating means is enabled by each said fixed length pulse to generate said second current during the duration of said fixed length pulse, and said first current and said second current having the same current amplitude.

4. The debris alarm of claim 3, wherein said fixed length pulse generating means comprises a one-shot having an input electrically coupled to said pulse threshold means and an output electrically coupled to said second current generating means.

5. The debris alarm according to claim 4, wherein said debris indicator means includes alarm means for emitting an operator perceivable signal.

6. The debris alarm according to claim 1, wherein said first current generating means provides said first current with one polarity and said second current generating means provides said second current with an opposite polarity and wherein said difference means includes an integrator to provide said difference voltage, said integrator having an input for receiving both said first currents and said second currents and wherein said window detector means is operative to determine that said integrator has been charged to a level so that said difference voltage falls outside said predetermined comparison window, said predetermined comparison window having said upper and lower threshold voltages which are preset fixed voltages.

7. The debris alarm according to claim 6, wherein said window detector means further includes first and second comparators, each said comparator having an input electrically coupled to an output of said integrator and an output electrically coupled to an input of said debris indicator means; said first comparator being operative to provide an enabling signal to said debris indicator means when said difference voltage from said integrator exceeds said positive threshold voltage and said second comparator being operative to provide an enabling signal to said debris indicator means when said difference voltage from said integrator falls below said lower negative threshold voltage.

8. The debris alarm according to claim 1, wherein said predetermined comparison window has said upper and lower threshold voltages which are variable threshold voltages, said threshold voltages being referenced to any one of said threshold pulses, said fixed length pulses and a combination of said threshold and fixed length pulses.

9. The debris alarm according to claim 8, wherein said current comparing means comprises a pair of integrators, one for receiving said threshold pulses and for generating a first voltage and the other for receiving said fixed length pulses and for generating a second voltage; a difference amplifier for receiving said first and second voltages and for providing as an output said difference voltage equal to the difference in said first and second voltage; means for obtaining a predetermined percentage of any one of said first voltage, second voltage, and a combination of said first voltage and second voltage, said percentage voltage being used as said lower and upper threshold voltage.

* * * * *